US006295125B1

United States Patent
Tokieda et al.

(10) Patent No.: US 6,295,125 B1
(45) Date of Patent: Sep. 25, 2001

(54) DIFFERENTIAL REFRACTIVE INDEX DETECTOR AND LIQUID CHROMATOGRAPH EQUIPPED WITH THE SAME

(75) Inventors: Tsunemi Tokieda; Yukio Nogami, both of Kawasaki; Saburo Inoue, Kawaguchi, all of (JP)

(73) Assignees: Showa Denko K.K., Tokyo; Erc Inc., Saitama-Ken, both of (JP)

(*) Notice: Subject to any disclaimer, the term of this patent is extended or adjusted under 35 U.S.C. 154(b) by 0 days.

(21) Appl. No.: 09/521,917

(22) Filed: Mar. 9, 2000

Related U.S. Application Data
(60) Provisional application No. 60/152,101, filed on Sep. 2, 1999.

(30) Foreign Application Priority Data

Jul. 23, 1999 (JP) .................................................. 11-209978

(51) Int. Cl.$^7$ .................................................. G01N 21/41
(52) U.S. Cl. ............................................................ 356/130
(58) Field of Search .................................... 356/130, 517, 356/128, 317; 210/198.2, 656, 659; 73/61.52

(56) References Cited

U.S. PATENT DOCUMENTS

| | | | | |
|---|---|---|---|---|
| 2,427,996 | * | 9/1947 | Seaman | 356/130 |
| 3,386,332 | * | 6/1968 | Watson | 356/130 |
| 3,539,263 | * | 11/1970 | Waters | 356/130 |
| 3,612,697 | * | 10/1971 | Nebe | 356/130 |
| 4,137,161 | * | 1/1979 | Shimada et al. | 210/198.2 |
| 5,157,454 | * | 10/1992 | Oka et al. | 356/130 |
| 5,168,325 | * | 12/1992 | Yoder-Short | 356/517 |
| 5,398,110 | * | 3/1995 | Kitaoka | 356/130 |
| 6,094,262 | * | 7/2000 | Almeida et al. | 356/130 |

FOREIGN PATENT DOCUMENTS

4024540 * 1/1992 (JP).

\* cited by examiner

Primary Examiner—Hoa Q. Pham
(74) Attorney, Agent, or Firm—Sughrue, Mion, Zinn, Macpeak & Seas, PLLC

(57) ABSTRACT

To provide a differential refractive index detector free from fears for occurrence of personal errors in the judgement of stable condition and capable of performing highly efficient analysis operation, and a liquid chromatograph equipped with the detector. A differential refractive index detector provided with a reference cell, a sample cell, a light source for irradiating light on these two cells, a detecting part for detecting light transmitted through respective cells, and a signal processing part for applying predetermined processing to the output signal from the detecting part, which comprises means for sequentially performing an initial solution purge operation of purging the sample cell and the reference cell with an eluent by passing the eluent through the cells at the start of operation of said detector, a stabilizing solution purge operation of allowing the eluent purge of sample cell and reference cell to proceed and at the same time, confirming the stable condition thereof, and a stability confirming operation of confirming whether or not the detector has stabilized in an analysis capable condition by passing the eluent only through the sample cell, and means for announcing that the detector has stabilized in the analysis capable condition. According to the differential refractive index detector of the present invention, the processing from the initial solution purge operation to the stability confirming operation can be automated and a highly efficient analysis operation can be attained.

9 Claims, 4 Drawing Sheets

DRIFT VALUE $(D_n) = (|d_n| + |d_{n-1}| + |d_{n-2}|)/3$
$d_n = V_n - V_{n-1}$, $d_{n-1} = V_{n-1} - V_{n-2}$, $d_{n-2} = V_{n-2} - V_{n-3}$

NOISE VALUE $(N_n) = (n_n + n_{n-1} + \cdots\cdots + n_{n-9})/10$

DIFFERENTIAL REFRACTIVE INDEX DETECTOR AND LIQUID CHROMATOGRAPH EQUIPPED WITH THE SAME

CROSS REFERENCE TO RELATED APPLICATIONS

This application is an application filed under 35 U.S.C. §111 (a) claiming benefit pursuant to 35 U.S.C. §119 (e)(1) of the filing date of the Provisional Application 60/152,101, filed Sep. 2, 1999, pursuant to 35 U.S.C. §111 (b).

BACKGROUND OF THE INVENTION

1. Technical field

The present invention relates to a differential refractive index detector and a liquid chromatograph equipped with the same.

More specifically, the present invention relates to a differential refractive index detector which can automatically perform the processing from the eluent purge operation of reference cell at the start of operation until the stability confirming operation by judging whether or not the detector was stabilized in an analysis capable condition, thereby enabling more efficient analysis work, and also relates to a liquid chromatograph equipped with the detector.

2. Related Art

FIG. 5 is a block diagram showing the outline of a conventional differential refractive index detector for a liquid chromatograph. As shown in FIG. 5, a conventional differential refractive index detector comprises two cells 11 and 12 consisting of a reference cell 11 for filling with or passage of a reference solution and a sample cell 12 through which a solution containing a sample is passed. These cells 11 and 12 are disposed such that their slant faces oppose each other. The sample cell 12 is connected by an eluent inlet line 14 for introducing an eluent eluted from a separation column 13 and by a sample cell outlet line 15. The reference cell 11 is connected by a reference cell inlet line 16 communicating with the sample cell outlet line 15 and by a reference cell outlet line 17.

At the connection between the reference cell outlet line 17 and a line 18 externally extended from the connection of the sample outlet line 15 with the reference cell inlet line 16, a three-way solenoid valve 19 is provided. To this three-way solenoid valve 19, an eluent outlet line 20 for discharging the eluent outside is connected. By intermittently switching over the three-way solenoid valve 19 on demand, the eluent which was flowed out from the sample cell 12 can be intermittently allowed to flow into the reference cell 11.

On one side with respect to the reference cell 11 and the sample cell 12, a light source 21 for irradiating a measuring beam is provided, and on the other side, a reflector 22 for reflecting the measuring beam transmitted through these cells 11 and 12 is provided. Furthermore, in the vicinity of the light source 21, a photoreceptor device for detecting the displacement of the measuring beam accompanying the difference in the refractive index of the eluent in the two cells 11 and 12 is provided.

The light source 21, the photoreceptor device 23 and the three-way solenoid valve 19 converge at a signal processing part 24. The signal processing part 24 has a function of outputting the difference in refractive index of the eluent into two cells 11 and 12 as an electric signal based on a signal sent from the photoreceptor device 23 and at the same time, controlling the driving of three-way solenoid valve 19 and the driving of light source 21 based on an operation signal sent from the outside.

In the conventional differential refractive index detector, electric power is charged and then start-up is initiated by an input unit not shown, as a result, the three-way solenoid valve 19 is actuated through the signal processing part 24 to bring a state such that the piping 18 is closed and the reference cell outlet line 17 communicates with the eluent outlet line 20.

Subsequently, the following operations are performed in sequence.

(1) Initial Solution Purge Operation

This is an operation of purging the inside of the reference cell 11 with an eluent at the start of operation of the differential refractive index detector.

(2) Stabilizing Solution Purge Operation

This is an operation of confirming whether factors other than the change of refractive index are in a stabilized condition by continuously passing an eluent which has flowed out from the sample cell 12, through the reference cell 11.

(3) Stability Confirming Operation

This is an operation of confirming whether or not the differential refractive index detector has stabilized in an analysis capable condition while keeping the flow passage in an analyzable condition by stopping the flow of eluent into the reference cell 11.

Through these operations, the differential refractive index detector can be stabilized in an analysis capable condition.

In the case where a conventional differential refractive index detector is used as a liquid chromatograph detector, the change in the refractive index of the eluent causes a serious problem. The refractive index of the eluent changes not only with the elution of a sample but also by the staining of eluent itself, the dissolved gas concentration, the temperature and the like. Accordingly, in order to stabilize the differential refractive index detector at the start of operation, unlike an ultraviolet absorbance detector which is a general liquid chromatograph detector, an initial solution purge operation of purging the referential cell 1 with a solution at the start of operation and subsequently stabilizing the solution purge operation, and stability confirming operation of monitoring the output signal (chromatogram) over a relatively long period of time until a stable condition is reached are necessary. Thus, much labor and a long period of time are disadvantageously required.

Furthermore, the judgement that the differential refractive index detector has reached a stable condition is made by intuition in many cases and greatly depends on the experience and skill of the judging person. This naturally brings about great personal errors in the judgement of stable condition. Depending on the case, the condition may be excessively stable or may be deficient in stability. Thus, this intuitive judgement is disadvantageous in that an efficient operation cannot be attained.

SUMMARY OF THE INVENTION

The present invention was developed in order to solve the problems described above. It is an object of the present invention to provide a differential refractive index detector in which the processing from an initial solution purge operation of intermittently introducing an eluent into a referential cell until a stability confirming operation of confirming that the differential refractive index detector has stabilized in an analysis capable condition are automated, thereby eliminating fears for personal errors in the judgement of stable condition and enabling a highly efficient analysis operation, and also to provide a liquid chromatograph equipped with the detector.

As a result of extensive investigations, the present inventors have found that the above-described objects can be attained by using a differential refractive index detector described below and a liquid chromatograph equipped with the detector. The present invention has been accomplished based on this finding.

More specifically, the present invention relates to the following matters.

The differential refractive index detector of the present invention, provided with a reference cell for filling or passing a reference solution, a sample cell for passing a solution containing a sample, a light source for irradiating light on the two cells, a detecting part for detecting light transmitted through the respective cells, and a signal processing part for applying a predetermined processing to the output signal sent from the detecting part, is characterized by comprising means for sequentially performing an initial solution purge operation of purging the sample cell and the reference cell with an eluent by passing the eluent through the cells at the start of operation of the detector, a stabilizing solution purge operation of allowing the eluent purge of the sample cell and the reference cell to proceed and at the same time, confirming the stable condition thereof, and a stability confirming operation of confirming whether or not the detector has stabilized in an analysis capable condition by passing the eluent only through the sample cell, and means for announcing that the detector has stabilized in the analysis capable condition.

According to the differential refractive index detector of the present invention, means for sequentially performing an initial solution purge operation of purging the sample cell and the reference cell with an eluent by passing the eluent through the cells at the start of operation of the detector, a stabilizing solution purge operation of allowing the eluent purge of the sample cell and the reference cell to proceed and at the same time, confirming the stable condition thereof, and a stability confirming operation of confirming whether or not the detector has stabilized in the analysis capable condition bypassing the eluent only through the sample cell, is provided, so that the processing from the initial solution purge operation to the stability confirming operation can be automated and a highly efficient analysis operation can be attained.

During the time period from the charging of electric power to the stabilization of detector in the analysis capable condition, operations and judgements by an operator are not necessary, therefore, fears for the operations and judgements being governed by the individual skill can be eliminated, as a result, the stable condition can be always kept at a constant level and more efficient analysis work can be attained.

Furthermore, means for announcing that the detector has stabilized in the analysis capable condition is provided, so that the operator can swiftly know that the detector has stabilized in the analysis capable condition and can efficiently perform the analysis work.

As such, the processing from the initial solution purge operation of introducing an eluent into a reference cell until the stability confirming operation of stabilizing the differential refractive index detector into the analysis capable condition can be automated and thereby a highly efficient analysis operation can be attained.

The liquid chromatograph of the present invention is characterized by being equipped with the differential refractive index detector of the present invention.

According to the liquid chromatograph of the present invention, a differential refractive index detector of the present invention is provided, so that the reference cell and the sample cell can be automatically and swiftly stabilized without any participation from an operator and the liquid chromatography can be more efficiently performed.

Furthermore, when the differential refractive index detector of the present invention is applied to a liquid chromatograph, the analysis operation of liquid chromatography can be performed with remarkably high efficiency.

DESCRIPTION OF PREFERRED EMBODIMENT

Hereinbelow, a preferred embodiment of the present invention will be concretely explained based on the figures, however, the present invention is by no means limited thereto.

Figure 1:
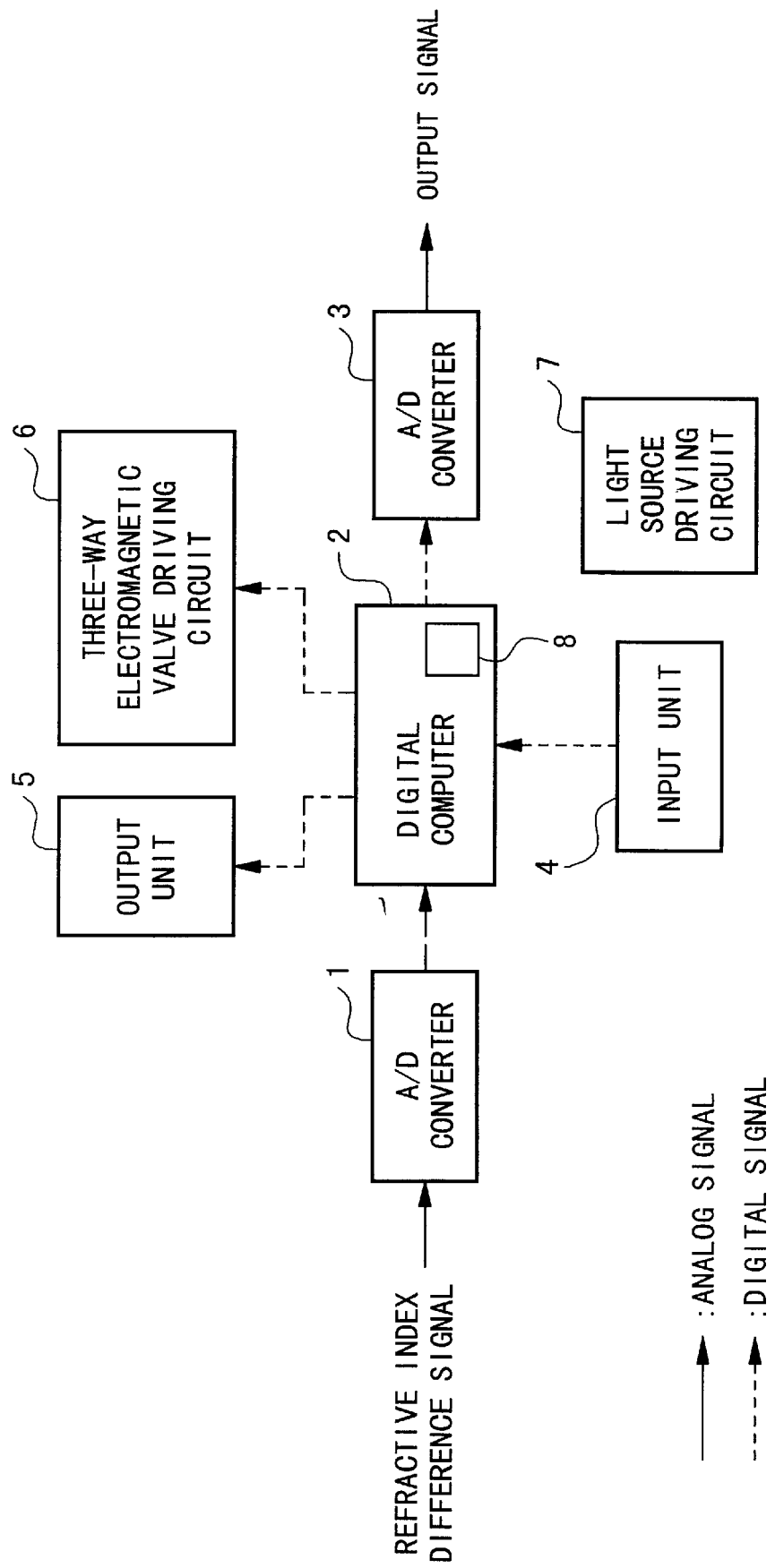
FIG. 1 is a block diagram showing the signal processing part forming an important part of a differential refractive index detector for a liquid chromatograph according to one embodiment of the present invention.

FIG. 1 is a block diagram showing the signal processing part forming an important part of a differential refractive index detector for a liquid chromatograph according to one embodiment of the present invention. In the figure, the numeral 1 is an A/D converter where an analog signal corresponding to the displacement of optical axis of light transmitted through a reference cell and a sample cell accompanying the difference in refractive index of the reference solution and the sample solution is output from the photoreceptor device (detection part) not shown and converted into a digital signal; 2 is a digital computer for applying predetermined processing on the digital signal output from the A/D converter 1; and 3 is a D/A converter where the digital signal as a result of processing is output from the digital computer and converted into an analog signal to output it as an output signal.

The numeral 4 is an input unit for inputting parameters such as respective limits of drift value and noise value or giving indications relating to the operations such as actuation or stopping and also for inputting input data or the like into the digital computer 2; 5 is an output unit for outputting the processing result output from the digital computer 2 with respect to the operating state, for example, whether or not the detector has stabilized in a analysis capable condition; 6 is a three-way solenoid valve driving circuit for driving a three-way solenoid valve by switching over the flow passage of eluent to the reference cell or sample cell; and 7 is a light source driving circuit for driving a light source not shown.

The output unit 5 has announcing means for announcing that the detector has stabilized in an analysis capable condition when it is confirmed in the stability confirming operation and also for announcing that the condition where the drift value described later is larger than the drift limit and/or the noise value is larger than the noise limit is continuing in excess of a predetermined time. The announcing means is a display unit such as display, an acoustic unit of making announcement by sound or an audio unit of making announcement by voice. Also, a unit of making the announcement by vibration or the like may be mounted as the announcing means.

The digital computer 2 stores a program (means) 8 as a previously established time series procedure.

According to this program 8, the following work is sequentially undertaken.

(1) Initial Solution Purge Operation

The eluent passed through the sample cell at the start of operation of detector is intermittently passed through the reference cell according to the previously established time series procedure to eliminate bubbles in the sample cell and the reference cell and also to roughly perform the eluent purge.

(2) Stabilizing Solution Purge Operation

After the completion of the initial solution purge operation, while keeping the eluent which has flowed out from the sample passing through the reference cell, a drift value and a noise value are determined from a signal corresponding to the difference in refractive index based on the signal sent from the photoreceptor device. These values are compared with a previously set drift limit and a noise limit and when the drift value is smaller than the drift limit and at the same time, the noise value is smaller than the noise limit, the eluent passed through the sample cell is stopped from passing through the reference cell. When the drift value is larger than the drift limit and/or the noise value is larger than the noise limit, the comparison operation is again performed.

(3) Stability Confirming Operation

While passing the eluent only through the sample cell, a drift value and a noise value are determined from a signal corresponding to the difference in refractive index based on the signal from the photoreceptor device. These values are compared with previously set drift limit and noise limit and when the drift value is smaller than the drift limit and at the same time, the noise value is smaller than the noise limit, the detector is judged to have stabilized in the analysis capable condition. When the drift value is larger than the drift limit and/or the noise value is larger than the noise limit, the comparison operation is again performed.

Figure 2:
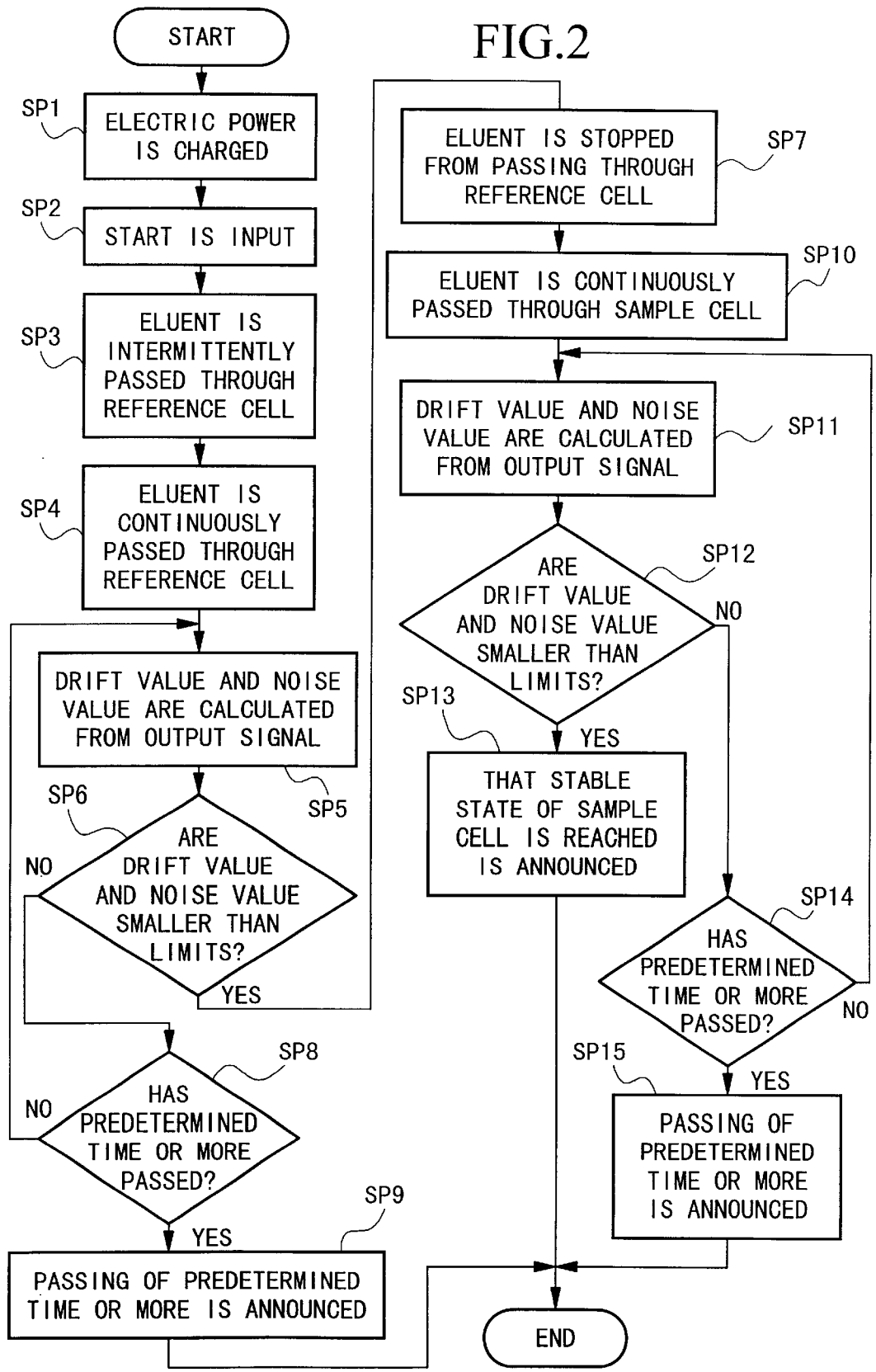
FIG. 2 is a flow chart showing works of a differential refractive index detector for a liquid chromatograph according to one embodiment of the present invention.

The working of the differential refractive index detector according to this embodiment is described below by referring to the flow chart shown in FIG. 2.

(1) Initial Solution Purge Operation

Electric power is charged (SP1) and when a START signal is inputted from the input unit 4 (SP2), the three-way solenoid valve driving circuit 6 is driven to flush the three-way solenoid valve and allow the eluent passed through from the sample cell to intermittently pass through the reference cell, whereby bubbles in the sample cell and the reference cell are eliminated and also rough eluent purge is attained (SP3).

(2) Stabilizing Solution Purge Operation

After the completion of initial solution purge operation, the three-way solenoid valve driving circuit is driven to open the three-way solenoid valve and continuously pass the eluent which has flowed out from the sample cell through the reference cell (SP4).

While keeping the eluent continuously passing through the reference cell, a drift value and a noise value are calculated by a signal corresponding to the difference in refractive index based on the signal sent from a photoreceptor device not shown (SP5).

Thereafter, the drift value and the noise value calculated are compared with the drift limit and the noise limit which are previously input by the input unit 4 (SP6).

At this time, when the drift value and the noise value both have become smaller than the limits, the three-way solenoid valve driving circuit 6 is driven to switch the flow passage and stop the flow of eluent into the reference cell (SP7).

When the drift value is larger than the drift limit and/or the noise value is larger than the noise limit in SP6, whether or not this state has continued in excess of a predetermined time (SP8) is determined. When the state is found not continuing in excess of a predetermined time, the works of from SP5 to SP6 is repeated, and when the state is determined to be continuing in excess of a predetermined time, the announcing means announces that a predetermined time or more has passed (SP9) and the work is terminated.

(3) Stability Confirming Operation

After the completion of the stabilizing solution purge operation, the eluent is continuously passed through the sample cell (SP10) and in this state, a drift value and a noise value are calculated from a signal corresponding to the difference in refractive index based on the signal sent from the photoreceptor device not shown (SP11). The drift value and the noise value calculated are compared with the drift limit and the noise limit previously input by the input unit 24 (SP12).

At this time, when the drift value and the noise value both have become smaller than respective limits, the announcing means announces that the detector has reached a condition capable of analysis (SP13) and the work is terminated.

When the drift value is larger than the drift limit and/or the noise value is larger than the noise limit in SP12, whether or not this state has continued in excess of a predetermined time (SP14) is determined. When the state is determined to be not continuing in excess of a predetermined time, the work of from SPE11 to SP12 is repeated, and when the state is determined to be continuing in excess of a predetermined time, the announcing means announces that a predetermined time or more has passed (SP15) and the works are terminated.

The methods for calculating the drift value and the noise value are described below.

Figure 3:
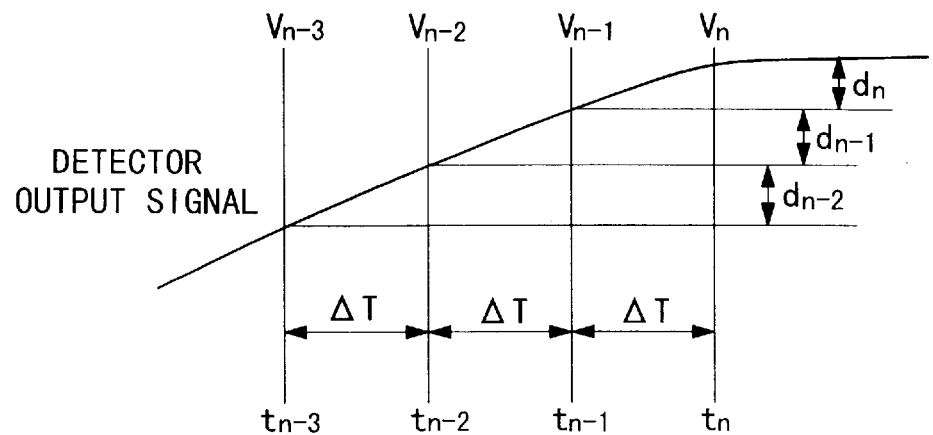
FIG. 3 is an explanatory view showing the calculation method of drift value in a differential refractive index detector for a liquid chromatograph according to one embodiment of the present invention.

In the calculation of the drift value, as shown in FIG. 3, an output signal value is measured at predetermined time intervals delta T (for example, from 3 to 15 minutes) and an absolute value of the difference between the output signal value at the time concerned and the output signal value at the preceding time is calculated and stored as the this-time value. In the same manner, the value calculated last time is stored as the last-time value, and the value calculated before last time is as the before-last-time value. A simple average of these this-time value, last-time value and before-last-time value is defined as the drift value at the time concerned.

Also, the drift value at the time concerned may be a smoothed value obtained using a smoothing constant. The output signal value at each measurement time may be an average of a plurality of measurements so as to reduce the dispersion in the measurement.

Figure 4:
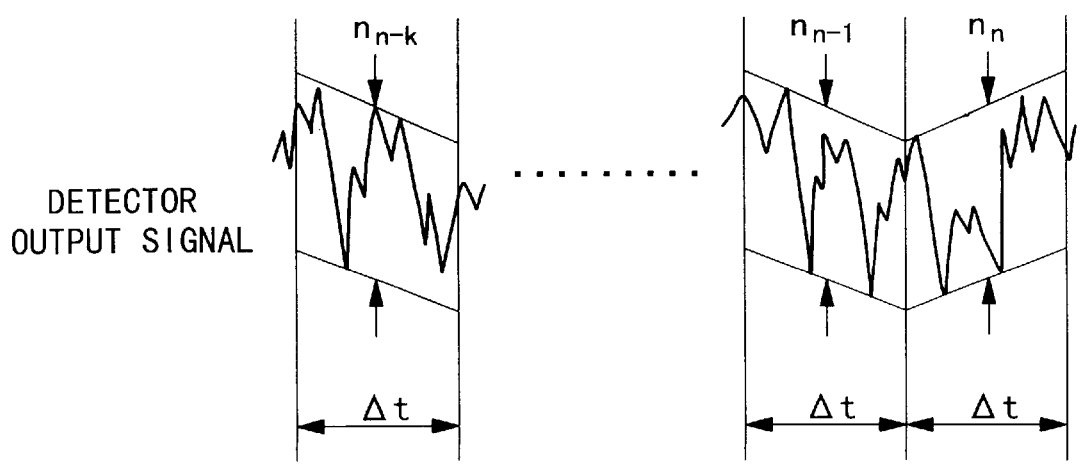
FIG. 4 is an explanatory view showing the calculation method of noise value in a differential refractive index detector for a liquid chromatograph according to one embodiment of the present invention.
Figure 5:
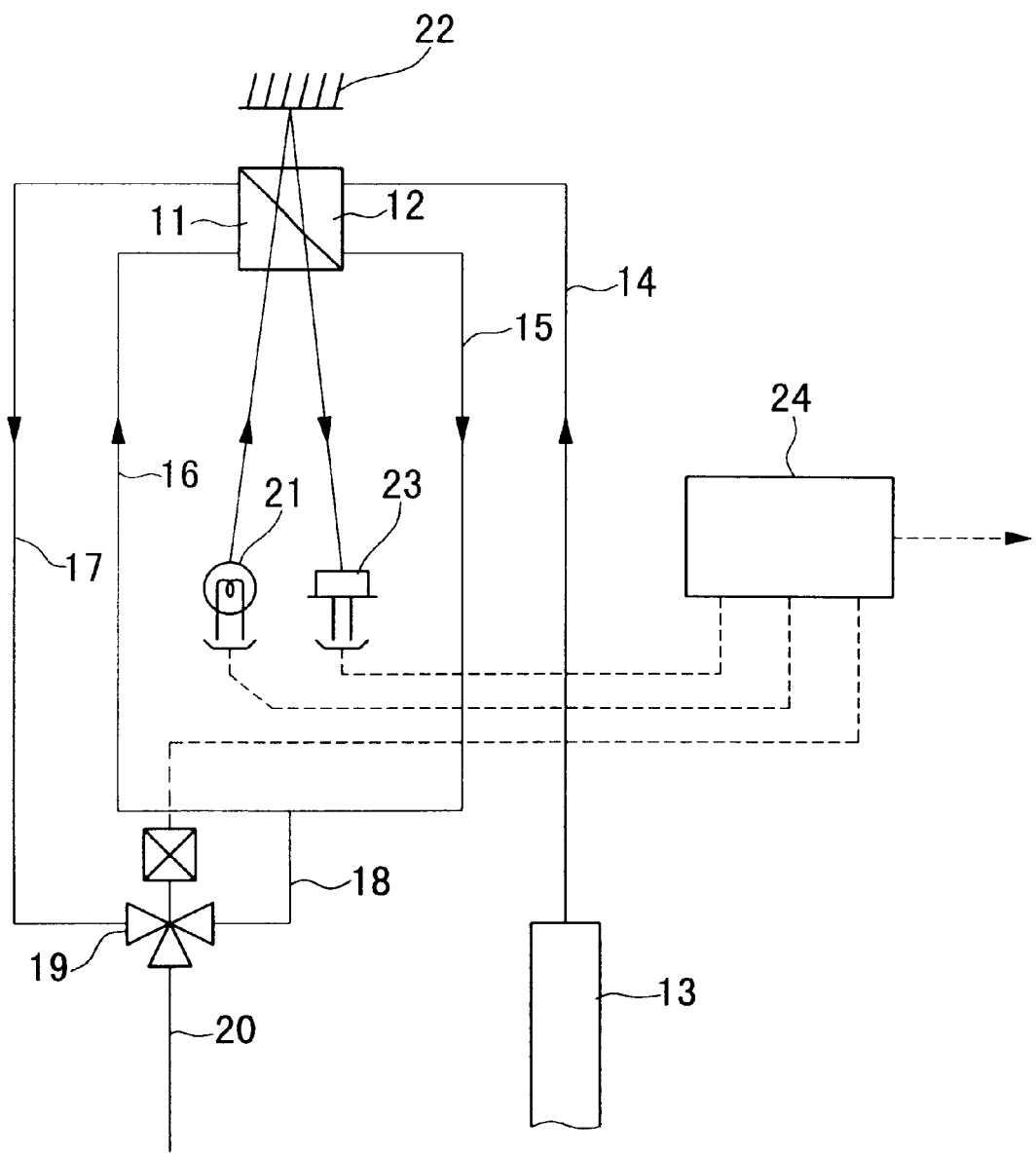
FIG. 5 is a block diagram showing a conventional differential refractive index detector for a liquid chromatograph.

In the calculation of the noise value, as shown in FIG. 4, instantaneous noise values are obtained in a plurality of blocks (k+1 blocks, wherein k is an integer satisfying, for example, $9 \leq k \leq 29$) divided at predetermined time intervals delta t (for example, from 0.5 to 1 minute) and an average of the instantaneous noise values obtained is defined as the noise value at the time concerned.

In the determination of the instantaneous noise value, as shown in FIG. 4, straight lines are drawn to include the minimum output signal value in a block and at the same time contact with one or more other output signal value. Out of these straight lines, a straight line having a smallest absolute value of gradient is picked up and on taking account of the relationship between this straight line and the output signal, a maximum value among absolute values of the difference at the same time instant is determined. Similarly, straight lines are drawn to include the maximum output signal value in a block and at the same time contact with one or more other output signal value. Out of these straight lines, a straight line having a smallest absolute value of gradient is picked up and on taking account of the relationship between this straight line and the output signal, a maximum value among absolute values of the difference at the same time instant is determined. A larger value of these values determined is defined as the instantaneous noise value of the block concerned. It is also possible to use a smaller value of the maximum values determined as the instantaneous noise value.

According to the differential refractive index detector of this embodiment, a program is stored in the digital computer 22, which is composed such that an initial solution purge operation of performing eluent purge by intermittently passing an eluent flown out from the sample cell through the reference cell at the start of operation of the detector, a stabilizing solution purge operation of allowing the eluent purge of the sample cell and the reference cell to proceed and at the same time, confirming the stable condition thereof, and a stability confirming operation of confirming whether or not said detector has stabilized in the analysis capable condition by passing the eluent only through the sample cell are sequentially undertaken. Therefore, the processing from the initial solution purge operation until the stability confirming operation can be automated and a highly efficient analysis operation can be attained.

During the time period from the charging of electric power to the stabilization of detector into the analysis capable condition, operations and judgements by an operator are dispensed with, therefore, fears for the operations and judgements being governed by the individual skill can be eliminated. As a result, the stable condition of factors except for the change of refractive index and the stable condition of the detector, that is, analysis capable condition, can be always kept at a constant level and more efficient analysis work can be attained.

Furthermore, when the differential refractive index detector of this embodiment is applied to a detector of liquid chromatograph, the detector can be automatically and swiftly stabilized without requiring any participation from an operator. Therefore, the analysis operation of liquid chromatography can be performed with remarkably high efficiency.

In the above, the differential refractive index detector according to one embodiment of the present invention is described with reffering to the drawings, however, the specific structure thereof is by no means limited to this embodiment and any change can be made in the design as long as it does not depart from the spirit and scope of the present invention.

For example, the width of predetermined time intervals delta T or delta t used in the calculation method of drift value or noise value, or the number of absolute values of difference used for the simple averaging may be appropriately changed according to the apparatus to which the detector is applied.

What is claimed is:

1. A differential refractive index detector provided with: a reference cell for filling or passing a reference solution, a sample cell for passing a solution containing a sample, a light source for irradiating light on said two cells, a detecting part for detecting light transmitted through respective cells, and a signal processing part for applying a predetermined processing to the output signal sent from said detecting part, wherein:

means for sequentially performing an initial solution purge operation of purging said sample cell and said reference cell with an eluent by passing the eluent through the cells at the start of operation of said detector, a stabilizing solution purge operation of allowing the eluent purge of said sample cell and said reference cell to proceed and at the same time, confirming the stable condition thereof, and a stability confirming operation of confirming whether or not said detector has stabilized in a analysis capable condition by passing said eluent only through said sample cell, and means for announcing that said detector has stabilized in the analysis capable condition.

2. A differential refractive index detector in accordance with claim 1, wherein in said initial solution purge operation, an eluent passed through said sample cell is intermittently passed through said reference cell according to a previously set time series procedure to eliminate bubbles in said reference cell and purge the cell with the eluent.

3. A differential refractive index detector in accordance with claim 1, wherein in said stabilizing solution purge operation, a drift value and a noise value are obtained from said output signal while maintaining the state where the eluent passed through said sample cell is passing through said reference cell, the values obtained are compared with previously set drift limit and noise limit, and when said drift value is smaller than said drift limit and at the same time, said noise value is smaller than said noise limit, the eluent passed through said sample cell is stopped from passing through said reference cell, or when said drift value is larger than said drift limit and/or said noise value is larger than said noise limit, the operation of obtaining said drift value and noise value and comparing these values is again performed.

4. A differential refractive index detector in accordance with claim 3, wherein said drift value is a value obtained by measuring the value of said output signal at predetermined time intervals, calculating an absolute value of the difference between the value of output signal at the time concerned and the value of output signal at the precedent time, and averaging the absolute values calculated.

5. A differential refractive index detector in accordance with claim 3, wherein said noise value is a value obtained by averaging respective instantaneous noise values of a plurality of blocks divided at predetermined time intervals.

6. A differential refractive index detector in accordance with claim 1, wherein in said stability confirming operation, a drift value and a noise value are obtained from said output signal while passing the eluent only through said sample cell, the values obtained are compared with previously set drift limit and noise limit, and when said drift value is smaller than said drift limit and at the same time, said noise value is smaller than said noise limit, said detector is judged to have stabilized in the analysis capable condition, or when said drift value is larger than said drift limit and/or said noise value is larger than said noise limit, the operation of obtaining said drift value and noise value and comparing these values is again performed.

7. A differential refractive index detector in accordance with claim 1, wherein means for announcing that the state where said drift value is larger than said drift limit and/or said noise value is larger than said noise limit has continued in excess of a predetermined time is provided.

8. A liquid chromatograph equipped with the differential refractive index detector provided with:

a reference cell for filling or passing a reference solution, a sample cell for passing a solution containing a sample, a light source for irradiating light on said two cells, a detecting part for detecting light transmitted through respective cells, and a signal processing part for applying a predetermined processing to the output signal sent from said detecting part, wherein:

means for sequentially performing an initial solution purge operation of purging said sample cell and said reference cell with an eluent by passing the eluent through the cells at the start of operation of said detector, a stabilizing solution purge operation of allowing the eluent purge of said sample cell and said reference cell to proceed and at the same time, confirming the stable condition thereof, and a stability confirming operation of confirming whether or not said detector has stabilized in a analysis capable condition by passing said eluent only through said sample cell, and means for announcing that said detector has stabilized in the analysis capable condition.

9. A method of measurement in a differential refractive index detector provided with a reference cell for filling or passing a reference solution, a sample cell for passing a solution containing a sample, a light source for irradiating light on said two cells, a detecting part for detecting light transmitted through respective cells, and a signal processing part for applying a predetermined processing to the output signal sent from said detecting part, for announcing that said detector has stabilized in an analysis capable condition, comprising the steps of:

a) sequentially performing an initial solution purge operation of purging said sample cell and said reference cell with an eluent by passing the eluent through the cells at the start of operation of said detector, b) stabilizing the solution purge operation of allowing the eluent purge of said sample cell and said reference cell to proceed and at the same time, c) determining whether it is in a stable condition, and a stability confirming operation of confirming whether or not said detector has stabilized in the analysis capable condition by passing said eluent only through said sample cell, d) announcing that said detector has stabilized in the analysis capable condition.

* * * * *